United States Patent [19]   [11] Patent Number: 5,337,376
Ravetti et al.                   [45] Date of Patent: Aug. 9, 1994

[54] CHEMICALLY SENSITIVE FIBER OPTIC CABLE

[75] Inventors: Robert G. Ravetti, Rancho Palos Verdes; Thomas K. Dougherty, Playa Del Rey, both of Calif.

[73] Assignee: Hughes Aircraft Company, Los Angeles, Calif.

[21] Appl. No.: 49,461

[22] Filed: Apr. 19, 1993

[51] Int. Cl.$^5$ .............................................. G02B 5/14
[52] U.S. Cl. ..................................... 385/12; 385/145; 250/227.14; 340/619
[58] Field of Search ................... 385/12, 13, 123, 128, 385/141, 145; 250/227.21, 227.23, 227.14, 905, 906, 907, 908; 340/603, 619, 870.28; 128/634

[56] References Cited

U.S. PATENT DOCUMENTS

| | | | |
|---|---|---|---|
| 4,133,915 | 1/1979 | Noethe et al. | 427/160 |
| 4,600,310 | 7/1986 | Cramp et al. | 385/123 X |
| 4,800,886 | 1/1989 | Nestor | 128/634 |
| 5,004,914 | 4/1991 | Vali et al. | 250/227.27 |
| 5,119,463 | 6/1992 | Vurek et al. | 385/129 |
| 5,250,095 | 10/1993 | Sigel, Jr. et al. | 385/12 X |

OTHER PUBLICATIONS

Patent Abstract of European Patent application 381612, Kritaman et al., Aug. 8, 1990.
Patent Abstract of European Patent application 312293, Kritzman et al., Apr. 19, 1989.
Japanese Patent Abstract, JP 02133338, Yokoshima et al., May 20, 1990.
G. Bruce Harper, "Reusable glass-bound pH indicators", Analytical Chemistry, vol. 47(2), 348-351 (1975) (Chem. Abstr., 92552a, vol. 82, p. 447, 1975).
A. L. Harmer, "Fibre Optic Chemical and Biochemical Sensors for Environmental Monitoring" in Optoelectronics for Environmental Science, S. Martellucci and A. N. Chester, Eds., Plenum Press (New York) pp. 39-43 (1989).
H. Hatanaka et al., "Preparation of vinyl polymers as pH inidcator", Makromol. Chem., vol. 175(6), (1974) (Chem. Abstr., 169881w, vol. 81. p. 2, 1974).

Primary Examiner—Rodney B. Bovernick
Assistant Examiner—Hemang Sanghavi
Attorney, Agent, or Firm—M. E. Lachman; M. W. Sales; W. K. Denson-Low

[57] ABSTRACT

A chemically sensitive sensor capable of detecting changes in concentrations of ions, atoms, or molecules in a fluid environment in which the sensor is immersed or embedded comprises a thin clad optical fiber, which is coated with a polymer which is permeable to liquids and which contains a chemically sensitive material, and a light carrying fiber. The polymeric material has the ability to change color and/or absorbance when the concentration of the ion, atom, or molecule in the surrounding environment changes. The polymer will return to its original color and/or absorbance state once the concentration goes back to the original value. The color change or absorbance is detected through the core of the optical fiber which is connected to a photodetector. The coupling of the light into the sensing structure is obtained by using a core-only optical fiber, surrounded by a clad material, in addition to an external light source. Coupling of the external light beam with the polymeric coated fiber is obtained through microbending losses in reverse by spooling the coated fiber around the clad material. Changes such as pH, metal or other ion concentration, organic molecule concentration, and gas molecule concentration may be detected.

18 Claims, 1 Drawing Sheet

CHEMICALLY SENSITIVE FIBER OPTIC CABLE

BACKGROUND OF THE INVENTION

1. Field of the Invention

The present invention is directed to sensors, and, more particularly, to chemical sensors useful in monitoring environmental pollutants.

2. Description of Related Art

European patent application 381612 entitled "Construction of a medical probe with bonded light sensitive compound and use thereof", published 8 Aug. 1990, describes the bonding onto porous glass of an oxygen sensitive molecule and then the coating of the glass with a silicone resin. The probe is used to measure oxygen concentration. The patent states it might also be used for the measurement of pH. However, work completed during the course of making the present invention showed that a coating such as disclosed in that reference (a silicone) was not sufficiently permeable to water and ions for this pH sensitivity application. Silicones do have high permeability to oxygen but not to water or hydrogen ions.

Glass bound pH indicators are described in a reference by Harper Bruce, "Reusable glass-bound pH indicators", *Analytical Chemistry*, Vol. 47(2), 348–351 (1975). However, there is no disclosure or suggestion that these indicators may be used in a fiber optic device.

Polymeric acid-base indicators are described in a publication by M. Tahan et al, "Synthesis of some polymeric dyes", *Isr J Chem*, 1971, 9 (2), 191–200. These are not described for optical coatings.

A review of fiber optic chemical and biochemical sensors for environmental monitoring is described by A. L. Harmer, "Fibre Optic Chemical and Biochemical Sensors for Environmental Monitoring" in *Optoelectronics for Environmental Science*, S. Martellucci and A. N. Chester, Eds., Plenum Press (New York), pp. 39–43 (1989).

No prior art in the packaging of devices for rugged applications such as the one described herein is known. Thus, there remains a need for a chemically sensitive sensor for environmental monitoring.

SUMMARY OF THE INVENTION

In accordance with the invention, a chemically sensitive sensor is provided for detecting changes in concentrations of ions or molecules. The sensor comprises:

(a) a light source portion including a light source;

(b) a light detector portion including means for detecting light;

(c) at least one probe portion; and (d) a fiber optic cable portion. The fiber optic portion comprises two optical fibers, a first optical fiber comprising a core-only fiber, connected between the means for detecting light and the probe portion, and a second optical fiber comprising a core and a cladding layer. The second optical fiber has a chemically sensitive coating thereon and is connected between the light source and the probe portion. Further, the second optical fiber is wound on the clad member of the probe portion. Each probe portion comprises a clad member surrounding a portion of the core-only fiber. The clad member has a higher index of refraction than that of the core-only fiber. The clad member supports on its outer surface a plurality of windings of the coated second optical fiber. Each probe portion also comprises a porous container surrounding the clad member for mechanically protecting the clad member while permitting fluids to penetrate to chemically react with the coating on the second fiber.

Also in accordance with the invention, a method of detecting changes in concentrations of molecules or ions in an environment containing fluids to be monitored comprises:

(a) providing the chemically sensitive sensor;

(b) exposing the probe portion of the sensor to the environment, whereby the fluids in the environment chemically react with the coating on the second fiber;

(c) turning on the light source to provide a source of light directed to the second fiber in the sensor through the clad member;

(d) measuring any light transmitted by the second fiber to the means for detecting light to generate a signal; and (e) determining the change in concentration of molecules or atoms or ions in the fluids from the signal.

The coating material on the second optical fiber is provided with the ability to change color or absorbance as the concentration of the species (molecule or ion) in the surrounding environment changes. The coating will return to the original color or absorbance again once the concentration returns to the original value. The color or absorbance change is detected through the core of the second optical fiber, which is connected to the light detecting means.

DESCRIPTION OF THE PREFERRED EMBODIMENTS

The present invention is directed to an optical fiber sensor capable of detecting changes in the concentration of molecules or ions in the environment in which the sensor is immersed or embedded. Examples of changes that may be detected by the sensor of the invention include pH, metal or other ion concentration, organic molecule concentration, gas molecule concentration, and the like. There may be a color change or a change in light absorbance associated with the change in concentration.

A thin clad optical fiber is coated with a polymer containing a chemically sensitive material which is permeable to liquids. This polymeric material has the ability to change color or absorbance when the concentration of the species being monitored in the surrounding environment changes. The polymer will return to its original color or absorbance again once the concentration of the species returns to its original value. The color change is detected through the core of the optical fiber which is connected to a spectrometer or, optionally, to a sensitive photodetector. The coupling of the light into the core is obtained by using a thin clad optical fiber in addition to an external light source. Coupling of the external light beam with the polymeric coated fiber is obtained through microbending losses in reverse by spooling the coated fiber around the clad material.

Figure 1:
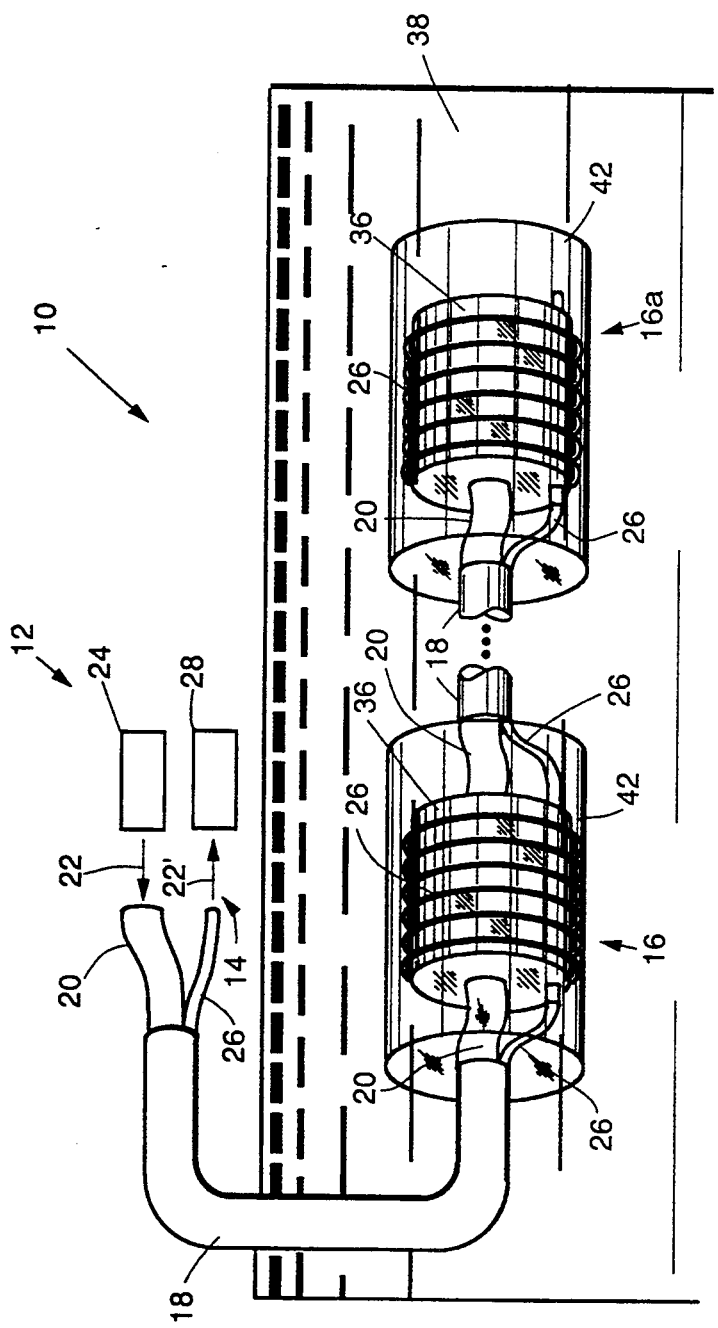
FIG. 1 is a schematic diagram, partly in perspective, of the sensor of the invention.

The sensor of the present invention is depicted in FIG. 1. The sensor 10 comprises a light source portion a light detector portion 14, a probe portion 16, and a fiber optic cable portion 18, which connects the light source portion and the light detector portion with the probe portion.

The light source portion 12 comprises a core-only fiber 20 transmitting high intensity light 22 provided by a light source 24. The light detector portion 14 comprises a coated sensor fiber 26 transmitting light 22' back to a detector 28. Both fibers 20, 26 together comprise the fiber optic cable portion 18.

Additional probes 16 can be connected together with more fiber optic cable 18 to cover lengths ranging from a few feet to several miles, as shown in FIG. 1, which depicts a second probe 16a connected in series to probe 16. In this manner, concentration changes may be sensed at different locations by using the same cable 18 when the light detector portion 14 includes an optical time domain refractometer (OTDR, not shown) for separating the multiple signals from the various probes 16, 16a, etc. Further, it will be appreciated that by providing a different chemically sensitive coating on each of the various probes 16, 16a, etc., a different species may be monitored.

Figure 2:
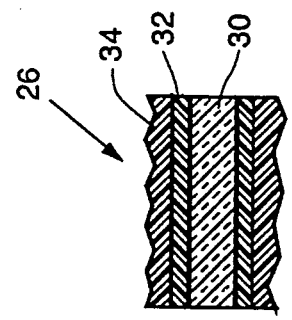
FIG. 2 is a cross-sectional view of a portion of a coated optical fiber comprising a portion of the sensor of FIG. 1.

FIG. 2 depicts in cross-section the coated optical fiber 26, which comprises a core 30, a cladding layer 32, and a coating 34. The core 30 and cladding layer 32 are conventional and do not, in themselves, form a part of this invention. The coating 34, which is chemically sensitive to a change in concentration of an atomic or molecular species, as delineated above, is described in greater detail below.

The fiber 26 with the chemically sensitive coating 34 is wrapped around a clad member, such as a clear plastic rod 36 which has the core-only optical fiber 20 passing through it. The clear plastic rod 36 is formed of a material having a higher index of refraction than that of the optical fiber 20. An example of such a material is poly(methyl acrylate), commercially available as Plexiglas. Light transmissive glasses, such as glass tubing 0.1 to 0.25 inch (0.25 to 0.62 cm) thick may alternatively be employed as the clad member 36.

Figure 3:
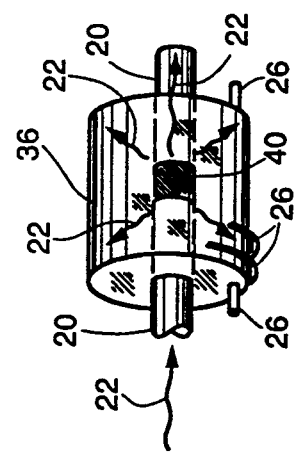
FIG. 3 is a perspective view of a portion of the sensor of FIG. 1, showing coupling of light from a core-only optical fiber to the coated optical fiber.

When the light 22 passes through the core-only fiber 20, it is dissipated in the higher refractive index clear plastic rod 36, as shown in FIG. 3, and it couples to the chemically sensitive fiber 26. If the chemical species being monitored in the environment 38 in which the probe 16 is located changes concentration, then the color of the coating 34 will change and the coupled light 22' will transmit this color change (or the change in light intensity) through the sensor fiber 26 back to the photodetector 28 (or spectrometer or OTDR).

Core-only fibers 20 may be connected within the plastic rod 36 by means of an optically clear epoxy 40. This enables splicing of the fibers 20 without loss of light transmission and provides a stronger splice by forming the plastic rod 36 around the optical fibers and the epoxy. Optically clear epoxies are well-known and commercially available.

A protective container 42 surrounding the probe, or sensing structure, 16 comprises a porous material, such as a glass or ceramic filter, preferably having a pore size in the range of about 1,000 to 25,000 $\mu$m. Alternatively, the protective container 42 may comprise a fine (0.5 to 10 mils, or 0.0012 to 0.025 cm) mesh cage, such as stainless steel. In any event, the purpose of the container 42 is to mechanically protect the sensing device 16 while allowing fluids from the environment 38 to pass into the sensing structure 16, to react with the coating 34.

The preparation of the coated optical fiber 26 involves the formulation, coating, and curing onto a glass fiber of a water permeable, indicator-containing polymer coating 34. Examples of such coatings are formulated by combining a water permeable polymer vehicle (which is not water soluble but is selected to be compatible with the other agents listed below and have some hydrophilicity), a mixture of monomeric and multifunctional polymerizable monomers selected to give a permeable, cross-linked coating that is stable to the environment, a chemically sensitive probe molecule that changes color and/or absorbance in response to a specific chemical agent, and a polymerization initiator. An example of such a coating 34 and its application to the optical fiber is now described. In this case, the coating contains phenolphthalein and is sensitive to pH changes in the environment.

Into dry oxygen-free tetrahydrofuran (1 ml) was placed high molecular weight polyvinyl acetate (0.4 g), acrylamide (0.4 g), methylenebisacrylamide (0.04 g), phenolphthalein (0.02 g), and azobisisobutrylnitrile (0.01 g). The solution was mixed well and then degassed with nitrogen. A glass fiber was then coated with the solution, and cured at 100° C. for 4 hours. The resulting coated fiber 26 was placed in an aqueous solution. The pH of the solution could be remotely sensed by measuring the amount of light 22' transmitted through the coated fiber 26 by a detector 28.

The coating 34 was permeable to water but maintained good adhesion to glass and was optically clear.

Examples of other coatings for fibers which have been found to be useful as chemically sensitive coatings in accordance with the present invention include the following:

pyrenebutyric acid (as disclosed in European Patent 381612, supra) for detecting pH and/or the partial pressure of oxygen and/or the partial pressure of carbon dioxide in body fluids;

perylene-3,9-dicarboxylic acid diisobutyl ester (as disclosed in European patent application 312293, 19 Apr. 1989) for detecting the partial pressure of oxygen;

polymeric dyes based on polyphenolphthalein or polyfluorescein (as disclosed in Isr. J. Chem., supra) as acid-base indicators; and vinyl polymers (as disclosed in Chem. Abstr., 169881w, Vol. 81, p. 2, 1974) as pH indicators.

In addition to the foregoing list of examples, there are many other examples, too numerous to mention here. However, the foregoing list will suffice to guide the practitioner skilled in the art in selecting other suitable chemically sensitive coatings for use in practicing the present invention.

The device 10 of the invention can be employed in remote sensing of environmental pollutants, such as in sensing chemical spills underground and contaminants in tanks. This device 10 is simple, sensitive, accurate, and inexpensive. In addition, this device unlike others, is durable because it is not made out of degradable or corrosive materials. Also, this device can sense pH concentrations at different locations by using the same cable when connected to an OTDR, as indicated above.

Various improvements to the invention may be made. For example, adhesion promoters may be used to provide better adhesion of glass to the coating. Another improvement is the use of other, more permeable monomers (for example, acrylic acid) in the coating formulation to improve permeability. Porosity may be induced in the coating to improve permeability. Also, the indicator molecule might be more stable if it were to be covalently bound to either the glass or the polymer. For example, the indicator molecule, or chemically-sensitive probe molecule, may include at least one functionality for participating in the polymerization reaction with the monomers and the polymerization initiator to provide the polymer coating with the chemically-sensitive probe molecule covalently bonded to the polymer coating.

Other indicators may also be employed in the practice of the invention. For example, different pH indicators may be used to sense different pH regions in the environment. Metal ion indicators and specific organic molecule indicators are also known. These may be incorporated into the coating 34 to sense these possible contaminants.

Thus, there has been disclosed a chemically sensitive fiber optic cable and device utilizing the same. It will be readily apparent to those skilled in this art that various changes and modifications of an obvious nature may be made, and all such changes and modifications are deemed to fall within the scope of the invention, as defined by the appended claims.

What is claimed is:

1. A chemically sensitive sensor adapted for detecting changes in concentrations of ions, atoms, or molecules in an environment containing fluids to be monitored, comprising:
   (a) a light source portion including a light source for generating light;
   (b) a light detector portion including means for detecting light;
   (c) at least one probe portion; and
   (d) a fiber optic portion comprising two optical fibers, wherein a first optical fiber comprises a core-only fiber connected between said means for detecting light and said at least one probe portion and a second optical fiber comprises a core, a cladding layer, and a chemically sensitive coating and is connected between said light source and said at least one probe portion, and said chemically sensitive coating comprises a water permeable, indicator-containing polymer coating, formulated from a water permeable polymer vehicle, a mixture of monomeric and multifunctional polymerizable monomers selected to give a permeable, cross-linked coating that is stable to the environment, a chemically sensitive probe molecule that changes at least one of color and absorbance in response to a specific chemical agent, and a polymerization initiator, wherein each said probe portion comprises:
   (1) a clad member surround a portion of said core-only fiber, said clad member having a higher index of refraction than that of said core-only fiber, said clad member supporting on its outer surface a plurality of windings of said second optical fiber; and
   (2) a porous or permeable protective container surrounding said clad member for mechanically protecting said clad member while permitting said fluid to penetrate said clad member to chemically react with said coating on said second optical fiber.

2. The chemically sensitive sensor of claim 1 wherein said clad member comprises a member selected from the group consisting of light transmissive glasses and plastics.

3. The chemically sensitive sensor of claim 2 wherein said clad member comprises poly(methyl acrylate).

4. The chemically sensitive sensor of claim 1 wherein said chemically sensitive probe molecule is sensitive to changes in at least one of the following: pH, metal or other ion concentration, organic molecule concentration, and gas molecule concentration.

5. The chemically sensitive sensor of claim 4 wherein said chemically sensitive probe molecule is sensitive to pH and said coating comprises phenolphthalein in a matrix comprising a cross-linked resin of polyvinyl acetate, acrylamide, methylenebisacrylamide, and azobisisobutrylnitrile.

6. The chemically sensitive sensor of claim 1 wherein said chemically-sensitive probe molecule is covalently bonded either to the surface of said second optical fiber or to said polymer coating.

7. The chemically sensitive sensor of claim 6 wherein said chemically-sensitive probe molecule includes at least one functionality for participating in a polymerization reaction with said monomers and said polymerization initiator to provide said polymer coating with said chemically-sensitive probe molecule covalently bonded to said polymer coating.

8. The chemically sensitive sensor of claim 1 wherein said protective container comprises a porous material comprising glass or ceramic.

9. The chemically sensitive sensor of claim 8 wherein said porous material has a pore size ranging from about 1,000 to 25,000 $\mu$m.

10. The chemically sensitive sensor of claim 1 wherein said protective container comprises a fine mesh cage having a mesh size of about 0.5 to 10 mils (0.0012 to 0.025 cm).

11. The chemically sensitive sensor of claim 10 wherein said protective container comprises a mesh of stainless steel.

12. A method of detecting changes in concentrations of ions, atoms, or molecules in an environment, comprising:
   (a) providing a chemically sensitive sensor comprising
      (1) a light source portion including a light source;
      (2) a light detector portion including means for detecting light;
      (3) at least one probe portion; and
      (4) a fiber optic cable portion, said fiber optic cable portion comprising two optical fibers, a first optical fiber comprising a core-only fiber connected between said means for detecting light and said at least one probe portion and a second optical fiber comprising a core and a cladding layer, said second optical fiber having a chemically sensitive coating thereon and connected between said light source and said at least one probe portion, and said chemically sensitive coating comprises a water permeable, indicator-containing polymer coating, which is formulated by reacting a water permeable polymer vehicle, a mixture of monomeric and multifunctional polymerizable monomers selected to give a permeable, cross-linked coating that is stable to the environment, a chemically sensitive probe molecule that changes at least one of color and absorbance in response to a specific chemical agent, and a polymerization initiator, wherein each said probe portion comprises:
  (i) a clad member surrounding a portion of said core-only fiber, said clad member having a higher index of refraction than that of said core-only fiber, said clad member supporting on its outer surface a plurality of windings of said coated second optical fiber; and
  (ii) a porous container surrounding said clad member for mechanically protecting said clad member while permitting fluids to penetrate to chemically react with said coating on said second fiber;
(b) exposing said at least one probe portion to said environment, whereby said fluids chemically react with said coating on said second fiber;
(c) turning on said light source to provide a source of light directed to said second fiber;
(d) measuring any light transmitted by said second fiber to said means for detecting light to generate a signal; and
(e) determining said change in concentration of ions, atoms, or molecules from said signal.

13. The method of claim 12 wherein said clad member comprises a member selected from the group consisting of light transmissive glasses and plastics.

14. The method of claim 13 wherein said clad member comprises poly(methyl acrylate).

15. The method of claim 12 wherein said chemically sensitive probe molecule is sensitive to changes in at least one of the following: pH, metal or other ion concentration, organic molecule concentration, and gas molecule concentration.

16. The method of claim 15 wherein said chemically sensitive probe molecule is sensitive to pH and said coating comprises phenolphthalein in a matrix comprising a cross-linked resin of polyvinyl acetate, acrylamide, methylenebisacrylamide, and azobisisobutrylnitrile.

17. The method of claim 12 wherein said protective container comprises a porous material comprising glass or ceramic having a pore size ranging from about 1,000 to 25,000 $\mu$m.

18. The method of claim 12 wherein said protective container comprises a fine mesh metal cage having a mesh size of about 0.5 to 10 mils (0.0012 to 0.025 cm).

* * * * *